US012565510B2

(12) United States Patent
Tomita et al.

(10) Patent No.: US 12,565,510 B2
(45) Date of Patent: Mar. 3, 2026

(54) PHOSPHOLIPID

(71) Applicant: NIPPON FINE CHEMICAL CO., LTD., Osaka (JP)

(72) Inventors: Koji Tomita, Takasago (JP); Yuki Inoue, Takasago (JP); Ayano Yokouchi, Takasago (JP); Sae Asayama, Takasago (JP); Naofumi Fukata, Takasago (JP)

(73) Assignee: NIPPON FINE CHEMICAL CO., LTD., Osaka (JP)

( * ) Notice: Subject to any disclaimer, the term of this patent is extended or adjusted under 35 U.S.C. 154(b) by 512 days.

(21) Appl. No.: 18/024,899

(22) PCT Filed: Jun. 2, 2022

(86) PCT No.: PCT/JP2022/022530

§ 371 (c)(1),
(2) Date: Mar. 6, 2023

(87) PCT Pub. No.: WO2022/259958

PCT Pub. Date: Dec. 15, 2022

(65) Prior Publication Data

US 2023/0312620 A1 Oct. 5, 2023

(30) Foreign Application Priority Data

Jun. 10, 2021 (JP) ................................ 2021-097190

(51) Int. Cl.
*C07F 9/10* (2006.01)
*A61K 9/127* (2025.01)
*A61K 47/28* (2006.01)
*A61K 48/00* (2006.01)
*C07F 9/6509* (2006.01)

(52) U.S. Cl.
CPC .............. *C07F 9/106* (2013.01); *A61K 9/127* (2013.01); *A61K 47/28* (2013.01); *A61K 48/00* (2013.01); *C07F 9/650952* (2013.01)

(58) Field of Classification Search
None
See application file for complete search history.

(56) References Cited

U.S. PATENT DOCUMENTS

2017/0119887 A1 5/2017 Nishikawa et al.

FOREIGN PATENT DOCUMENTS

| | | | |
|---|---|---|---|
| EP | 3611178 | A1 | 2/2020 |
| JP | 2016-23147 | A | 2/2016 |
| WO | 2010/055340 | A1 | 5/2010 |
| WO | 2021/048868 | A1 | 3/2021 |
| WO | 2022/054955 | A1 | 3/2022 |

OTHER PUBLICATIONS

Hirai, Y. et al., Charge-reversible lipid derivative: A novel type of pH-responsive lipid for nanoparticle-mediated siRNA delivery, International Journal of Pharmaceutics, vol. 585, p. 1-10, 2020, XP086208599 (10 pages); cited in Extended European Search Report dated Jul. 3, 2025.

Extended (supplementary) European Search Report dated Jul. 3, 2025, issued in counterpart EP Application No. 22820140.6 (6 pages).

International Search Report dated Jul. 12, 2022, issued in counterpart International Application No. PCT/JP2022/022530. (2 pages).

CAS Registry No. 2389048-38-6. Database Registry. online. Dec. 10, 2019, [retrieval date Jun. 24, 2022]. retrieved from: STN. (1 page).

*Primary Examiner* — Celeste A Roney

(57) ABSTRACT

The present invention provides a charge-reversible phospholipid that is not positively charged at a pH of the body fluid (typically in the neutral range) and has low cytotoxicity.

The present invention provides a phospholipid represented by formula (1):

(1)

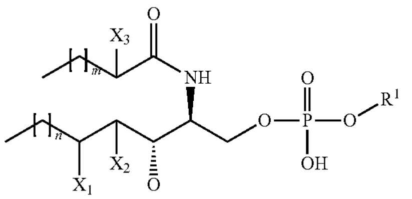

wherein m represents a natural number of 9 to 25, n represents a natural number of 10 to 15, $X_1$, $X_2$, and $X_3$ are the same or different and each represent H or OH, and $R^1$ represents the following formula (i) or (ii):

(i)

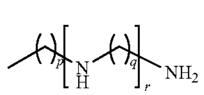

wherein p represents 1 or 2, q represents 1 or 2, and r represents an integer of 1 to 4; or (ii)

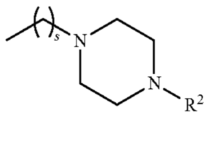

wherein s represents an integer of 1 to 3, and $R^2$ represents a hydrogen atom or a hydrocarbon group.

12 Claims, 6 Drawing Sheets

PHOSPHOLIPID

TECHNICAL FIELD

The present invention relates to phospholipids and the like.

BACKGROUND ART

In recent years, pharmaceuticals containing small interfering RNA (siRNA) and genetic vaccines containing messenger RNA (mRNA) have been under development. An extremely sophisticated delivery system is required for externally administered RNA to exhibit its intrinsic activity in vivo. This is because RNA is readily degraded by nucleases, and poorly penetrates cell membranes. Thus, the commercial viability of RNA-containing pharmaceuticals and vaccines inevitably involves the development of a delivery system.

A known delivery system for medicinal substances, such as RNA, is administration of a medicinal substance encapsulated in a lipid particle. However, administering a negatively charged nucleic acid typically involves the use of a positively charged lipid to cause electrostatic interaction; this raises concerns regarding cytotoxicity (PTL 1).

CITATION LIST

Patent Literature

PTL 1: JP2016-023147A

SUMMARY OF INVENTION

Technical Problem

The present inventors focused on the fact that a charge-reversible phospholipid has siRNA encapsulation properties and safety at a physiological pH. The present inventors also focused on the fact that when the charge-reversible phospholipid is a lipid particle that is not positively charged at a pH of the body fluid (typically in the neutral range), it can reduce cytotoxicity.

An object of the present invention is to provide a charge-reversible phospholipid that is not positively charged at a pH of the body fluid (typically in the neutral range) and has low cytotoxicity. Preferably, an object of the present invention is to further provide a lipid particle of a size that can efficiently encapsulate a medicinal substance and/or that is suitable for efficient delivery of a medicinal substance; and to provide a lipid for forming the lipid particle.

Solution to Problem

The present inventors conducted extensive research, and found that the above object can be achieved by a phospholipid having a specific structure. Thus, the present invention has been completed.

Specifically, the present invention relates to the following phospholipid and the like.

1. A phospholipid represented by formula (1):

(1)

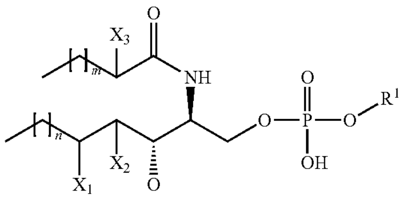

wherein m represents a natural number of 9 to 25, n represents a natural number of 10 to 15, $X_1$, $X_2$, and $X_3$ are the same or different and each represent H or OH, and $R^1$ represents the following formula (i) or (ii):

(i)

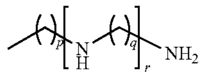

wherein p represents 1 or 2, q represents 1 or 2, and r represents an integer of 1 to 4; or (ii)

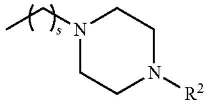

wherein s represents an integer of 1 to 3, and $R^2$ represents a hydrogen atom or a hydrocarbon group.

2. The phospholipid according to Item 1, wherein m represents a natural number of 13 to 21, and n represents a natural number of 11 or 12.
3. The phospholipid according to Item 1, represented by the following formula (2):

(2)

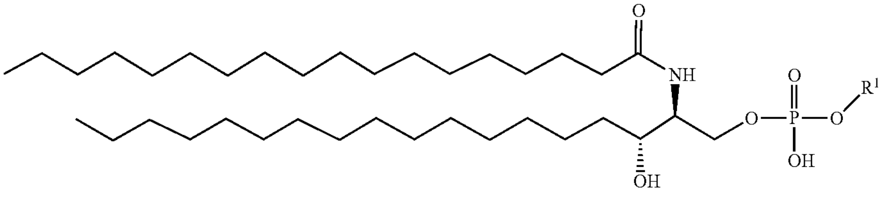

wherein $R^1$ is as defined above.

4. A lipid particle comprising the phospholipid according to Item 1 (phospholipid A).
5. The lipid particle according to Item 4, in which a medicinal substance is encapsulated.
6. The lipid particle according to Item 5, wherein the medicinal substance is a polynucleotide.
7. The lipid particle according to Item 4, comprising a sterol.
8. The lipid particle according to Item 4, further comprising a phospholipid other than phospholipid A (phospholipid B).
9. An alcohol solution comprising the phospholipid according to Item 1.
10. The alcohol solution according to Item 9, wherein an alcohol in the alcohol solution is ethanol.
11. A method for producing a lipid particle, the method comprising mixing the alcohol solution according to Item 9 with an acidic aqueous solution.
12. A medical drug comprising the lipid particle according to Item 4.

The present invention also relates to the following phospholipid and the like.

1. A phospholipid represented by formula (1):

(1)

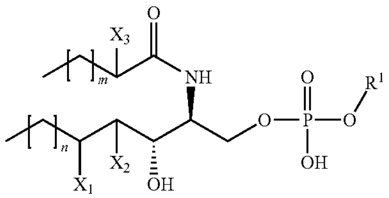

wherein m represents a natural number of 9 to 25, n represents a natural number of 10 to 15, $X_1$, $X_2$, and $X_3$ are the same or different and each represent H or OH, and $R^1$ represents the following formula (i) or (ii):

(i)

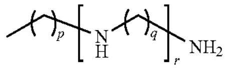

wherein p represents 1 or 2, q represents 1 or 2, and r represents an integer of 1 to 4; or (ii)

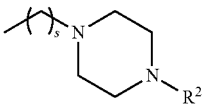

wherein s represents an integer of 1 to 3, and $R^2$ represents a hydrogen atom or a hydrocarbon group.

2. The phospholipid according to Item 1, wherein m represents a natural number of 13 to 21, and n represents a natural number of 11 or 12.
3. The phospholipid according to Item 1 or 2, represented by the following formula (2):

(2)

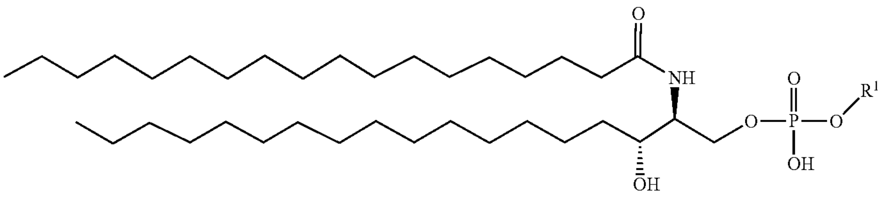

wherein $R^1$ is as defined above.

4. A lipid particle comprising the phospholipid according to any one of Items 1 to 3 (phospholipid A).
5. The lipid particle according to Item 4, in which a medicinal substance is encapsulated.
6. The lipid particle according to Item 5, wherein the medicinal substance is a polynucleotide.
7. The lipid particle according to any one of Items 4 to 6, comprising a sterol.
8. The lipid particle according to any one of Items 4 to 7, further comprising a phospholipid other than phospholipid A (phospholipid B).
9. An alcohol solution comprising the phospholipid according to any one of Items 1 to 3.
10. The alcohol solution according to Item 9, wherein an alcohol in the alcohol solution is ethanol.
11. A method for producing a lipid particle, the method comprising mixing the alcohol solution according to Item 9 or 10 with an acidic aqueous solution.
12. A medical drug comprising the lipid particle according to any one of Items 4 to 8.

Advantageous Effects of Invention

The phospholipid of the present invention is charge reversible, is not positively charged at a pH of the body fluid (typically in the neutral range), and has low cytotoxicity.

DESCRIPTION OF EMBODIMENTS

Figure 1:
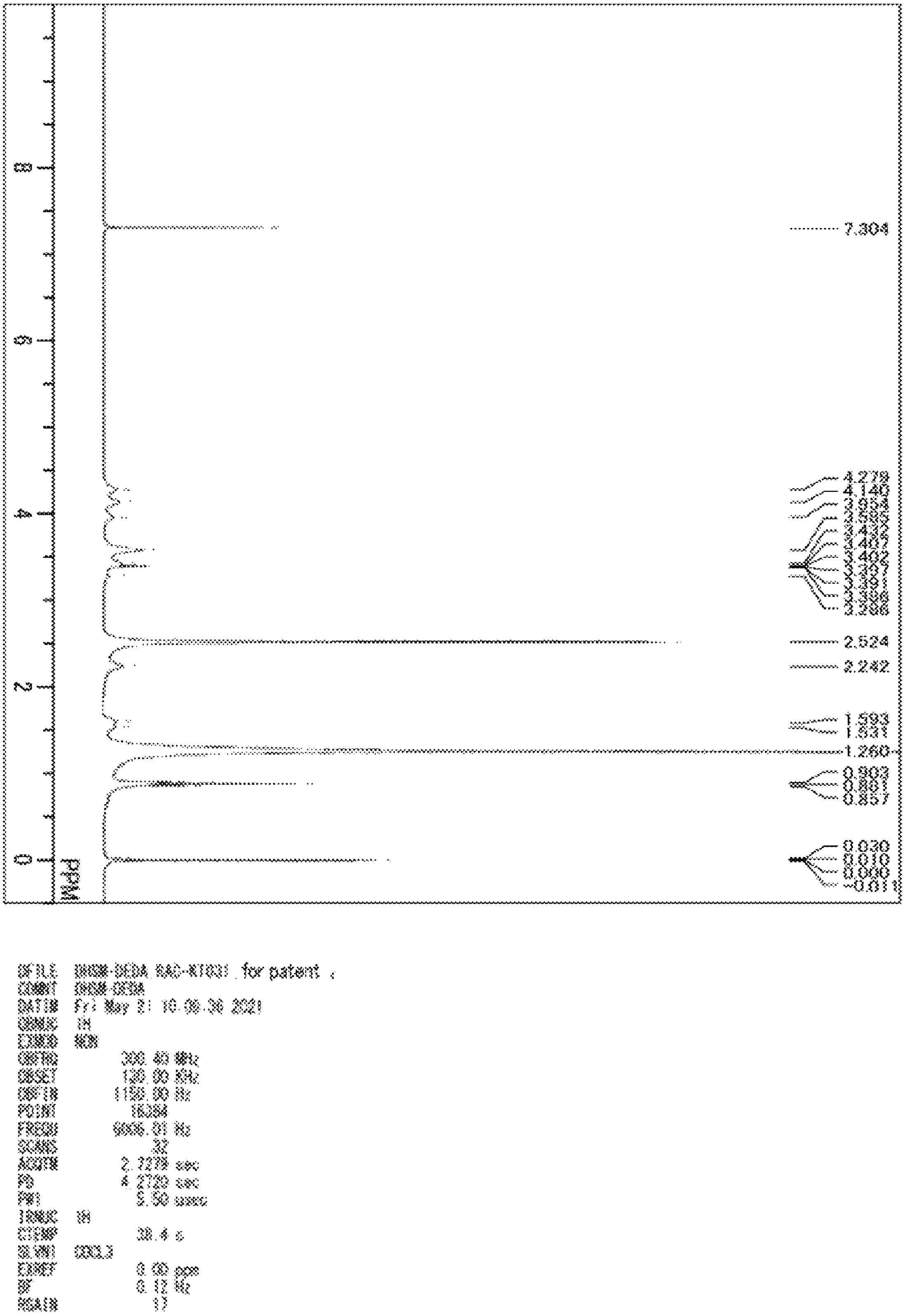
FIG. 1 shows an NMR chart of DHSM-DEDA synthesized in Example 1.

In this specification, the terms "comprise," "contain," and "include" include the concepts of "comprise," "contain," "include," "consist essentially of," and "consist of."

1. Lipid-Containing Composition

The present invention, according to one embodiment thereof, relates to a phospholipid represented by formula (1):

(1)

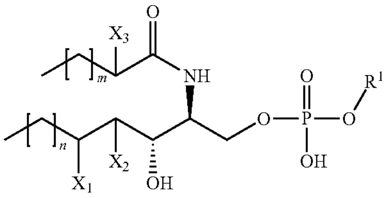

wherein m represents a natural number of 9 to 25, n represents a natural number of 10 to 15, $X_1$, $X_2$, and $X_3$ are the same or different and each represent H or OH, and $R^1$ represents the following formula (i) or (ii):

(i)

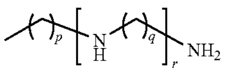

wherein p represents 1 or 2, q represents 1 or 2, and r represents an integer of 1 to 4; or (ii)

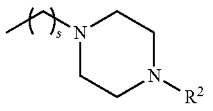

wherein s represents an integer of 1 to 3, and $R^2$ represents a hydrogen atom or a hydrocarbon group (which may be referred to as "the phospholipid of the present invention" in this specification). The following describes this phospholipid.

In formula (1), m represents a natural number of 9 to 25, and n represents a natural number of 10 to 15. m is preferably a natural number of 13 to 21, more preferably a natural number of 14 to 18, and still more preferably 15. n is preferably a natural number of 11 or 12, and more preferably 12. It is more preferable that m is a natural number of 13 to 21, and that n is a natural number of 11 or 12.

In formula (1), $X_1$, $X_2$, and $X_3$ are the same or different and each represent H or OH; preferably, $X_1$, $X_2$, and $X_3$ each represent H.

The phospholipid of the present invention is preferably a compound represented by the following formula (2):

(2)

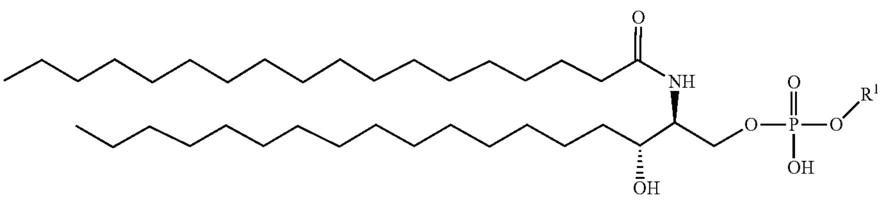

In formula (2), $R^1$ is the same as $R^1$ in formula (1).

In formulas (1) and (2), $R^1$ represents the following formula (i) or (ii):

(i)

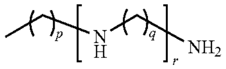

(ii)

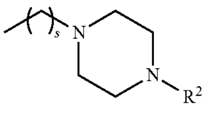

In formula (i), p represents 1 or 2, and q represents 1 or 2. p is preferably 2. q is preferably 2. Further, p and q are both preferably 2.

In formula (i), r represents an integer of 1 to 4. From the standpoint of more excellent low cytotoxicity, r is preferably 1. From the standpoint of further enhancing the encapsulation efficiency of a medicinal substance, r is preferably 2.

In formula (ii), s represents an integer of 1 to 3. s is preferably 2.

In formula (ii), $R^2$ represents a hydrogen atom or a hydrocarbon group. The hydrocarbon group represented by $R^2$ is not particularly limited, as long as it is a monovalent hydrocarbon group. The hydrocarbon group is preferably a chain hydrocarbon group, and more preferably an alkyl group. The number of carbon atoms in the hydrocarbon group is not particularly limited, and is, for example, 1 to 8, preferably 1 to 6, more preferably 1 to 4, still more preferably 1 or 2, and particularly preferably 1.

$R^2$ is preferably a hydrogen atom or an alkyl group, and more preferably a hydrogen atom.

The phospholipid of formula (1) also includes salt forms. The salt can be an acidic salt or a basic salt. Examples of acidic salts include inorganic acid salts, such as hydrochloride, hydrobromide, sulfate, nitrate, and phosphate; and organic acids, such as acetate, propionate, tartrate, fumarate, maleate, malate, citrate, methanesulfonate, and para-toluenesulfonate. Examples of basic salts include alkali metal salts, such as sodium salts and potassium salts; alkaline earth metal salts, such as calcium salts and magnesium salts; salts with ammonia; and salts with organic amines, such as morpholine, piperidine, pyrrolidine, monoalkylamine, dialkylamine, trialkylamine, mono(hydroxyalkyl)amine, di(hydroxyalkyl)amine, and tri(hydroxyalkyl)amine.

The phospholipid of the present invention can be synthesized by various methods. The compound of the present invention can be synthesized, for example, in accordance with or with reference to the following reaction scheme:

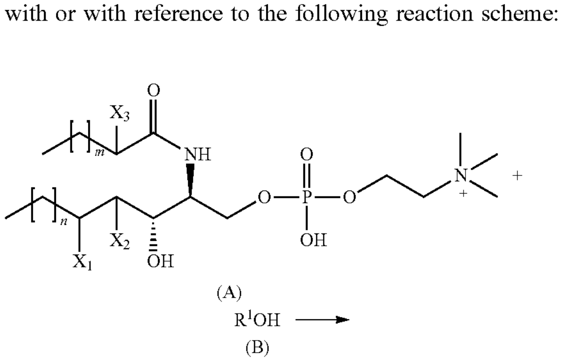

-continued

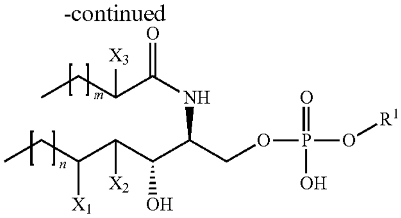

(1)

wherein m, n, $X_1$, $X_2$, $X_3$, and $R^1$ are as defined above.

In this reaction, the compound represented by formula (A) is reacted with the compound represented by formula (B) in the presence of a known enzyme, such as phospholipase D, thereby preparing the compound represented by formula (1).

From the standpoint of yield etc., the amount of the compound represented by formula (B) for use is preferably 1 mol or more, more preferably 2 mol or more, still more preferably 4 mol or more, and particularly preferably 8 mol or more, per mol of the compound represented by formula (A). From the standpoint of yield etc., the amount of the compound represented by formula (B) for use is preferably 20 mol or less, more preferably 16 mol or less, and still more preferably 14 mol or less, per mol of the compound represented by formula (A).

This reaction is performed in the presence of a solvent. The solvent is not particularly limited, as long as the solvent can help the enzyme exert its activity. The solvent preferable for use includes various buffers. A preferable buffer is an acetate buffer. The solvent preferably has a pH of 4 to 7, and more preferably 5 to 6. This reaction system may contain various organic solvents for dissolving the compound represented by formula (A) (e.g., chloroform), in addition to the aqueous solvent.

This reaction is typically performed by mixing a solution of the compound represented by formula (A) in an organic solvent with a solution of the compound represented by formula (B) in an aqueous solvent, and adding an enzyme to the mixture.

In this reaction, additives, in addition to the components described above, may also be suitably used to the degree that the progress of the reaction is not significantly interfered with.

The reaction temperature is not particularly limited, as long as the temperature allows the enzyme to exert its activity. The reaction temperature is typically 20 to 50° C., and preferably 35 to 45° C.

The reaction time is not particularly limited, as long as the reaction time allows the enzyme to exert its activity. The reaction time is typically 6 hours to 72 hours, and preferably 12 hours to 24 hours.

After completion of the reaction, the solvents are evaporated off, and the product can be isolated and purified by typical techniques, such as chromatography and recrystallization. The structure of the product can be identified, for example, by element analysis, MS (FD-MS) analysis, IR analysis, $^1$H-NMR, or $^{13}$C-NMR.

To improve lipid nanoparticle safety, ionizable lipids have been developed and nanoparticulated. Ionizable lipids are positively charged in the acidic range, and the change in net electrical charge in that case is 0→+1. However, the change in net electrical charge of the phospholipid of the present invention (charge-reversible lipid) can be within the range of −1 to +2; the viewpoint is different. The phospholipid of the present invention is even ionized under neutral conditions, and differs from ionizable lipids in physicochemical properties. Because the lipid of the present invention is able to behave as an amphipathic lipid under neutral conditions, the lipid can offer the prospect of higher stability and higher safety.

The use of the phospholipid of the present invention enables the formation of a lipid particle that is not positively charged at a pH of the body fluid (typically in the neutral range), and that enables efficient onset of the effect of a medicinal substance encapsulated in the lipid particle.

2. Lipid Particle

The present invention, according to one embodiment thereof, relates to a lipid particle (in this specification, "the lipid particle of the present invention") containing the phospholipid of the present invention (in this specification, "phospholipid A"). The following describes this lipid particle.

The lipid particle of the present invention is not particularly limited, as long as it contains the phospholipid of the present invention as a component lipid of the particle. The phospholipid of the present invention contained in the lipid particle may be one type alone, or a combination of two or more types. The lipid particle of the present invention is, for example, formed such that an amphipathic lipid containing the phospholipid of the present invention forms the outer layer, and the lipid molecules are lined with their hydrophilic portions facing outward. Examples of the lipid particle include particles having the outer layer formed from a lipid monolayer membrane, and particles having the outer layer formed from a lipid bilayer membrane. The lipid particle is preferably a particle having the outer layer formed from a lipid monolayer membrane, and more preferably a particle having the outer layer formed from a lipid monolayer membrane in which amphipathic lipid molecules are lined with their hydrophilic portions facing outward. The inner layer of the particle may be composed of a homogeneous aqueous phase or a homogeneous oil phase, and the inner layer preferably contains one or multiple reverse micelles.

The particle size of the lipid particle of the present invention is not particularly limited. The particle size is preferably nanosize, and is specifically, for example, 10 to 700 nm, preferably 20 to 500 nm, more preferably 40 to 200 nm, and still more preferably 60 to 150 nm.

The lipid particle of the present invention is preferably not positively charged at a pH of the body fluid (typically in the neutral range).

The lipid particle of the present invention may contain other lipids as a lipid component of the particle, in addition to the phospholipid of the present invention. Specific examples of such lipids include phospholipids, glycolipids, sterols, and saturated or unsaturated fatty acids.

Specific examples of phospholipids include phosphatidylcholines, such as dilauroylphosphatidylcholine, dimyristoylphosphatidylcholine, dipalmitoylphosphatidylcholine, distearoylphosphatidylcholine, dioleoylphosphatidylcholine, dilinoleoylphosphatidylcholine, myristoylpalmitoylphosphatidylcholine, myristoylstearoylphosphatidylcholine, and palmitoylstearoylphosphatidylcholine; phosphatidylglycerols, such as dilauroylphosphatidylglycerol, dimyristoylphosphatidylglycerol, dipalmitoylphosphatidylglycerol, distearoylphosphatidylglycerol, dioleoylphosphatidylglycerol, dilinoleoylphosphatidylglycerol, myristoylpalmitoylphosphatidylglycerol, myristoylstearoylphosphatidylglycerol, and palmitoylstearoylphosphatidylglycerol; phosphatidylethanolamines, such as dilauroylphosphatidylethanolamine, dimyristoylphosphatidylethanolamine, dipalmitoylphosphatidylethanolamine, distearoylphosphatidylethanolamine, dioleoylphosphatidylethanolamine, dilinoleoylphosphatidylethanolamine, myristoylpahmitoylphosphatidylethanolamine, myristoylstearoylphosphatidylethanolamine, and palmitoylstearoylphosphatidylethanolamine; phosphatidylserine; phosphatidic acid; phosphatidylinositol; sphingomyelin; cardiolipin; egg yolk lecithin; soybean lecithin; and hydrogenated products thereof. These phospholipids may be those modified with a water-soluble polymer, such as PEG.

Specific examples of glycolipids include glyceroglycolipids, such as diglycosyl diglyceride, digalactosyl diglyceride, galactosyl diglyceride, and glycosyl diglyceride; glycosphingolipids, such as galactosyl cerebroside and ganglioside; and stearyl glucoside and esterified stearyl glycoside.

Specific examples of sterols include cholesterol, cholesteryl hemisuccinate, lanosterol, dihydrolanosterol, desmosterol, dihydrocholesterol, phytosterol, phytosterol, stigmasterol, timosterol, ergosterol, sitosterol, campesterol, and brassicasterol. The lipid particle preferably contains a sterol as a lipid component of the liposome membrane, particularly because of its action to stabilize the liposome membrane, and to adjust the fluidity of the liposome membrane.

Specific examples of saturated or unsaturated fatty acids include saturated or unsaturated fatty acids having 10 to 22 carbon atoms, such as decanoic acid, myristic acid, palmitic acid, stearic acid, arachidonic acid, oleic acid, and docosanoic acid.

These lipids may be used singly, or in a combination of two or more.

The lipid particle of the present invention preferably contains a phospholipid other than the phospholipid of the present invention (in this specification, "phospholipid B"), and/or a sterol, and more preferably phospholipid B and a sterol. According to one embodiment of the present invention, when the phospholipid of the present invention has an unsaturated chain hydrocarbon group, phospholipid B preferably has a saturated chain hydrocarbon group. Phospholipid B is preferably phosphatidylcholine, and particularly preferably dipalmitoyl phosphatidylcholine. Other examples of phospholipid B include distearoylphosphatidylcholine, dimyristoylphosphatidylcholine, dioleoylphosphatidylcholine, palmitoyloleoylphosphatidylcholine, and the like. The sterol is preferably cholesterol.

When the lipid particle of the present invention contains phospholipid B, phospholipid B is present in an amount of, for example, 15 to 100 mol, preferably 30 to 70 mol, more preferably 40 to 60 mol, and still more preferably 45 to 55 mol, per 100 mol of the phospholipid of the present invention. Alternatively, phospholipid B is present in an amount of, for example, 5 to 70 mol, preferably 10 to 40 mol, more preferably 15 to 30 mol, and still more preferably 17 to 27 mol, per 100 mol of the phospholipid of the present invention. Alternatively, phospholipid B is present in an amount of, for example, 400 to 500 mol, preferably 420 to 480 mol, more preferably 430 to 470 mol, and still more preferably 445 to 455 mol, per 100 mol of the phospholipid of the present invention.

When the lipid particle of the present invention contains a sterol, the sterol is present in an amount of, for example, 30 to 200 mol, preferably 60 to 140 mol, more preferably 80 to 120 mol, still more preferably 90 to 110 mol, and still yet more preferably 95 to 105 mol, per 100 mol of the phospholipid of the present invention. Alternatively, the sterol is present in an amount of, for example, 250 to 600 mol, preferably 300 to 500 mol, more preferably 340 to 480 mol, still more preferably 430 to 470 mol, and particularly preferably 445 to 455 mol, per 100 mol of the phospholipid of the present invention.

When the lipid particle of the present invention contains phospholipid B and a sterol, phospholipid B is present in an amount of, for example, 15 to 100 mol, preferably 30 to 70 mol, more preferably 40 to 60 mol, and still more preferably 45 to 55 mol, per 100 mol of the sterol. Alternatively, phospholipid B is present in an amount of, for example, 5 to 70 mol, preferably 10 to 40 mol, more preferably 15 to 30 mol, and still more preferably 17 to 27 mol, per 100 mol of the sterol. Alternatively, phospholipid B is present in an amount of, for example, 70 to 140 mol, preferably 80 to 130 mol, more preferably 90 to 120 mol, and still more preferably 95 to 105 mol, per 100 mol of the sterol.

The phospholipid of the present invention and optionally added other lipids (in a preferable embodiment, phospholipid B and a sterol) are present in a total amount of, for example, 50 mol, or more, preferably 70 mol % or more, more preferably 90 mol % or more, still more preferably 95 mol % or more, and still yet more preferably 99 mol % or more, per 100 moli of the lipid component of the lipid particle of the present invention.

In the lipid particle of the present invention, part of the phospholipid can be modified with a water-soluble polymer, such as PEG. A phospholipid modified with PEG is present in an amount of, for example, 0 to 50 mol %, preferably 0 to 30 mol %, more preferably 0 to 20 mol %, and still more preferably 0 to 15 mol %, per 100 mol % of the lipid component of the lipid particle of the present invention.

In the lipid particle of the present invention, a medicinal substance is preferably encapsulated. The medicinal substance is not particularly limited, and examples include polynucleotides, peptides, proteins, carbohydrates, and low-molecular compounds. The medicinal substance is preferably negatively charged, and preferably water-soluble. Such a medicinal substance suitably usable is a polynucleotide. The target disease of the medicinal substance is not particularly limited, and examples include cancer (in particular, solid cancer).

The polynucleotide is not particularly limited, as long as the polynucleotide can function as a medicinal substance. Examples include siRNA, miRNA, antisense nucleic acids, mRNA, expression vectors therefor, expression vectors for proteins, and nucleic acids for genome editing (e.g., guide RNAs, Cas protein expression vectors, and TALEN expression vectors).

The polynucleotide may have a known chemical modification as described below. To prevent degradation by hydrolases such as nucleases, the phosphoric residue (phosphate) of each nucleotide may be replaced with a chemically modified phosphoric residue, such as phosphorothioate (PS), methylphosphonate, or phosphorodithionate. The hydroxyl group at position 2 of the sugar (ribose) of each ribonucleotide may be replaced with —OR (R represents, for example, $CH_3$ (2'-O-Me), $CH_2CH_2OCH_3$ (2'-O-MOE), $CH_2CH_2NHC(NH)NH_2$, $CH_2CONHCH_3$, or $CH_2CH_2CN$). Additionally, the base moiety (pyrimidine, purine) may be chemically modified; for example, introduction of a methyl group or a cationic functional group into position 5 of the pyrimidine base, or replacement of the carbonyl group at position 2 into thiocarbonyl. The phosphoric moiety or hydroxyl moiety may also be modified with, for example, a biotin, an amino group, a lower alkyl amine group, or an acetyl group. However, chemical modification is not limited thereto. Additionally, BNA (LNA), for example, whose sugar moiety conformation is immobilized in N form by bridging the 2'oxygen and 4'carbon in the sugar moiety of the nucleotide, can also be preferably used.

The medicinal substance is preferably contained in the inner layer of the lipid particle of the present invention. When the medicinal substance is a polynucleotide, the medicinal substance is preferably contained within a reverse micelle in the inner layer.

The molar ratio of the lipid component of the lipid particle of the present invention to the medicinal substance (the lipid component of the lipid particle of the present invention/the medicinal substance, mol/mol) is, for example, 500 or more, preferably 1000 or more, more preferably 1500 or more, still more preferably 1900 or more, still yet more preferably 2500 or more, and particularly preferably 3200 or more, when, for example, the medicinal substance is a polynucleotide, such as siRNA. The upper limit of the molar ratio is not particularly limited, and is, for example, 10000, 7000, or 5000.

The lipid particle of the present invention may contain other components in addition to the components described above. Examples of other components include membrane stabilizers, charged substances, antioxidants, membrane proteins, polyethylene glycol (PEG), antibodies, peptides, and sugar chains.

An antioxidant can be added to prevent oxidation of the membrane, and is optionally used as a component of a membrane. Examples of antioxidants used as a component of a membrane include butylated hydroxytoluene, propyl gallate, tocopherol, tocopheryl acetate, mixed tocopherol concentrate, vitamin E, ascorbic acid, L-ascorbyl stearate, ascorbyl palmitate, sodium hydrogen sulfite, sodium sulfite, sodium edetate, erythorbic acid, and citric acid.

A membrane protein can be added to add functions to a membrane, or to stabilize the structure of a membrane, and is optionally used as a component of a membrane. Examples of membrane proteins include peripheral membrane proteins, integral membrane proteins, albumin, and recombinant albumins.

The other components are present in an amount of, for example, 10% or less, preferably 5% or less, more preferably 2% or less, and still more preferably 1% or less, based on 100 mass % of the lipid particle of the present invention.

The lipid particle of the present invention can be produced in accordance with or with reference to a known production method for a lipid particle. The lipid particle of the present invention can be produced preferably by a method including the step of mixing an alcohol solution containing the phospholipid of the present invention with an acidic aqueous solution (step 1).

The alcohol as a solvent of the alcohol solution is not particularly limited, as long as the alcohol can dissolve the phospholipid. From the standpoint of solubility, the alcohol is preferably ethanol, 2-propanol, t-butanol, or the like. Of these, ethanol is particularly preferably used, from the standpoint of easy handling, safety, etc.

The acidic aqueous solution typically contains an acid in addition to water, which is a solvent. Examples of the acid include organic acids and inorganic acids, with organic acids being preferable. Examples of organic acids include maleic acid, formic acid, acetic acid, propionic acid, folic acid, isobutyric acid, valeric acid, isovaleric acid, pyruvic acid, oxalic acid, malonic acid, succinic acid, glutaric acid, ketoglutaric acid, adipic acid, lactic acid, tartaric acid, fumaric acid, oxaloacetic acid, malic acid, isocitric acid, citric acid, benzoic acid, phthalic acid, isophthalic acid, terephthalic acid, hemimellitic acid, trimellitic acid, trimesic acid, mellophanic acid, prehnitic acid, pyromellitic acid, mellitic acid, methanesulfonic acid, benzenesulfonic acid, p-toluenesulfonic acid, camphorsulfonic acid, p-toluenesulfinic acid, and benzenesulfinic acid; with citric acid being preferable.

Examples of inorganic acids include hydrochloric acid, sulfuric acid, nitric acid, carbonic acid, boric acid, boronic acid, hydrofluoric acid, hypochlorous acid, chlorous acid, chloric acid, perchloric acid, hypobromous acid, bromous acid, bromic acid, perbromic acid, hypoiodous acid, iodous acid, iodic acid, periodic acid, phosphorus acid, phosphoric acid, polyphosphoric acid, chromic acid, permanganic acid, and Amberlyst. The acids may used singly, or in a combination of two or more.

The acidic aqueous solution preferably has a pH of 3 to 5.

The acidic aqueous solution preferably contains a water-soluble medicinal substance.

The mixture ratio of the acidic aqueous solution to the alcohol solution (the acidic aqueous solution/the alcohol solution, v/v) is, for example, 1.5 to 10, preferably 2 to 8, and more preferably 3 to 6.

Mixing is not particularly limited, as long as the mixing mode allows the phospholipid to be mixed with the medicinal substance. For example, the acidic aqueous solution and the alcohol solution can be intensely stirred with a vortex mixer or the like. Although the mixing time period varies depending on the mixing mode, the mixing time period is, for example, 10 seconds to 2 minutes, and preferably 15 seconds to 1 minute.

Step 1 can be performed, for example, at ordinary temperature, or can also be performed with heating. The temperature in step 1 is, for example, 5° C. to 50° C., and preferably 15° C. to 45° C. When t-butanol is not used or when a small amount of t-butanol is used, lipid particles can be prepared even if the temperature in step 1 is relatively low. The temperature is, for example, less than 30° C., or 25° C. or less.

Step 1 can also be performed using a reaction system with a microchannel. In this case, the conditions for step 1 can be suitably adjusted according to the reaction system.

After step 1, it is preferable to remove alcohol by dialysis. Water can be generally used as the dialysis solvent. The dialysis time is, for example, 4 to 48 hours, preferably 6 to 24 hours, and more preferably 6 to 12 hours. It is preferable to exchange the dialysis solvent as appropriate during dialysis.

The lipid particle of the present invention may be a frozen product, a freeze-dried product, or the like.

3. Application of Lipid Particle

The present invention, according to one embodiment thereof, relates to a medical drug containing the lipid particle of the present invention (in this specification, "the medical drug of the present invention"). The lipid particle of the present invention is also usable as a reagent.

The lipid particle of the present invention enables a medicinal substance (e.g., a polynucleotide, such as siRNA) to exert its effect more efficiently, while reducing cytotoxicity. Thus, the lipid particle of the present invention can suitably be used as a carrier for a medicinal substance.

The content of the active ingredient (i.e., a medicinal substance) in the medical drug of the present invention can be suitably determined, taking into consideration, for example, the type of target disease, target therapeutic effect, administration method, treatment period, patient's age, and patient's body weight. For example, the content of the active ingredient in the medical drug of the present invention may be about 0.0001 parts by weight to 100 parts by weight, based on the entire medical drug of the present invention taken as 100 parts by weight.

The mode of administration of the medical drug of the present invention is not particularly limited, as long as a desired effect is brought about. The medical drug can be administered to mammals including humans through an administration route of either peroral administration or parenteral administration (e.g., intravenous injection, intramuscular injection, subcutaneous administration, rectal administration, transdermal administration, and local administration). The mode of administration is preferably parenteral administration, and more preferably intravenous injection. The dosage forms for peroral administration and parenteral administration and the production methods therefor are well known to those skilled in the art. Such dosage forms can be produced by mixing an active ingredient with a pharmaceutically acceptable carrier and other components, in accordance with a standard method.

The dosage form for parenteral administration includes injectable preparations (e.g., drip injectable drugs, intravenous injectable drugs, intramuscularly injectable drugs, subcutaneously injectable drugs, and intradermally injectable drugs), drugs for external use (e.g., ointments, cataplasms, and lotions), suppository inhalants, eye drops, ophthalmic ointments, nasal drops, and ear drops. For example, an injectable preparation can be prepared by dissolving the lipid particle of the present invention in injectable distilled water, and a solubilizing agent, a buffer, a pH adjuster, a tonicity agent, a soothing agent, a preservative, a stabilizer etc., can be optionally added thereto. The medical drug may be a freeze-dried formulation that is prepared into a drug when needed.

The medical drug of the present invention may further contain other medicinal agents effective in the treatment or prevention of diseases. The medical drug of the present invention may also optionally contain components, such as antiseptic drugs, antiphlogistics, cell activators, vitamins, and amino acids.

For the carrier for use in preparing the medical drug of the present invention, those typically used in this technical field, such as excipients, binders, disintegrants, lubricants, colorants, and flavoring agents, can be used; and stabilizers, emulsifiers, absorption promoters, surfactants, pH adjusters, antiseptics, antioxidants, fillers, moisturizers, surface activators, dispersants, buffers, preservatives, solubilizing agents, soothing agents, and the like can also optionally be used.

The dosage of the medical drug of the present invention can be determined by a practical physician, taking into consideration various factors, such as the administration route; type of disease; degree of symptoms; patient's age, gender, and body weight; severity of disease; pharmacological findings such as pharmacokinetics and toxicological characteristics; whether a drug delivery system is used; and whether the medical drug is administered as part of a combination with other medicinal substances. The dosage of the medical drug of the present invention may be, for example, about 1 μg/kg (body weight) to 10 g/kg (body weight) per day. The dose schedule of the medical drug of the present invention can also be determined while taking into consideration the same factors as those for the dosage. For example, the medical drug of the present invention can be administered in the dosage per day described above once daily to once per month.

EXAMPLES

The following describes the present invention in detail with reference to Examples. However, the present invention is not limited to these Examples.

Synthesis Example 1: Synthesis of DHSM-DEDA and DHSM-PPZ (2S,3R)-3-hydroxy-2-stearamidooctadecyl (2-(2'-aminoethylenamine)ethyl) phosphate (DHSM-DEDA: Example 1) and (2S,3R)-3-hydroxy-2-stearamidooctadecyl (2-(piperazino)ethyl) phosphate (DHSM-PPZ: Example 2) were synthesized in accordance with the following scheme.

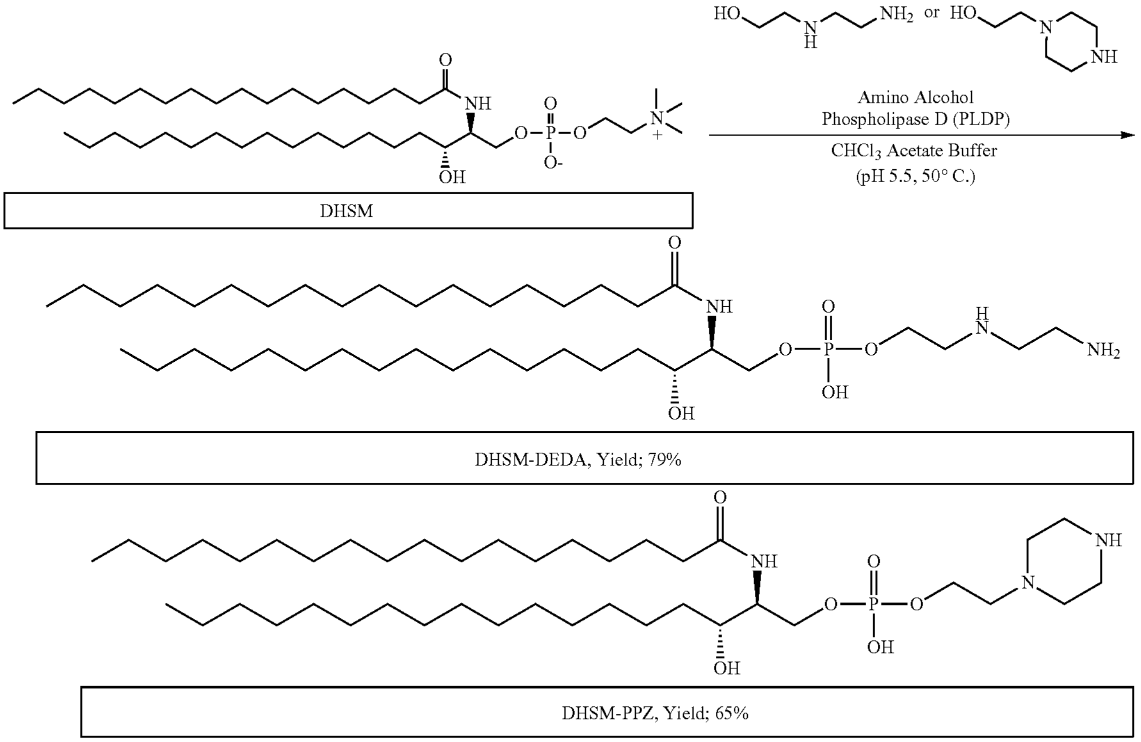

DHSM
DHSM-DEDA, Yield; 79%
DHSM-PPZ, Yield; 65%

Example 1: Synthesis of DHSM-DEDA

A 0.5M acetate buffer with a pH of 5.5 in which 5.54 g of 2-(2-aminoethylamino)ethanol (53 mmol) was dissolved was added to a mixture prepared by dissolving 3.00 g (4.1 mmol) of DHSM in chloroform, and this mixture was heated to 50° C. After heating, phospholipase D (1,440 U) was added thereto, followed by stirring for 16 hours. The mixture was stirred until consumption of DHSM was confirmed by TLC analysis. In this specification, one unit is defined as an enzyme amount with which 1 micro-mol (μmol) of a substrate is changed per minute (1 micro-mol per minute) under optimum conditions (an acidity at which the chemical reaction proceeds most at a temperature of 30° C.).

The reaction mixture was diluted with methanol, and washed with a 20% sodium chloride aqueous solution while heating to 50° C. The organic phase was concentrated under reduced pressure, and concentrated to dryness, thereby obtaining 5.75 g of a concentrate. 3.04 g of the obtained crude reaction product was dissolved in 55.0 g of chloroform, methanol, and water (chloroform:methanol:water=60:30:5 (vol/vol)), 16 mL of EtOH/1.25M HCl was added dropwise thereto, and the filtrate was stirred with ice-cooling for 30 minutes. The white crystal precipitated after stirring was filtered, and the crystal was suspended and washed with acetone three times. The obtained crystal was vacuum-dried overnight, thereby obtaining 2.15 g of a white crystal. 21.5 g of chloroform and methanol (chloroform:methanol=2:1 (vol/vol)) was added to the entire amount of the obtained white crystal, and the mixture was heated to 60° C. to dissolve the crystal, followed by filtration through a 0.2-μm membrane. After cooling, the mixture was stirred at room temperature for 1 hour. The white crystal precipitated after stirring was filtered, and the crystal was suspended and washed with chloroform and methanol (chloroform:methanol=2:1 (vol/vol)). The obtained crystal was vacuum-dried overnight, thereby obtaining 1.25 g of a white crystal (yield: 79%). FIG. 1 shows an NMR chart.

Example 2: Synthesis of DHSM-PPZ 2.80 g (3.82 mmol) of DHSM was dissolved in chloroform, and to the resulting solution, a 0.5M acetate buffer with a pH of 5.5 in which 6.90 g of 1-(2-hydroxyethyl) piperazine (53 mmol) was dissolved was added, and this mixture was heated to 50° C. After heating, phospholipase D (1,440 U) was added thereto, followed by stirring at 40° C. After 17 hours, elimination of DHSM was confirmed by TLC. One unit is defined as an enzyme amount with which 1 micro-mol (μmol) of a substrate is changed per minute (1 micro-mol per minute) under optimum conditions (an acidity at which the chemical reaction proceeds most at a temperature of 30° C.).

Figure 2:
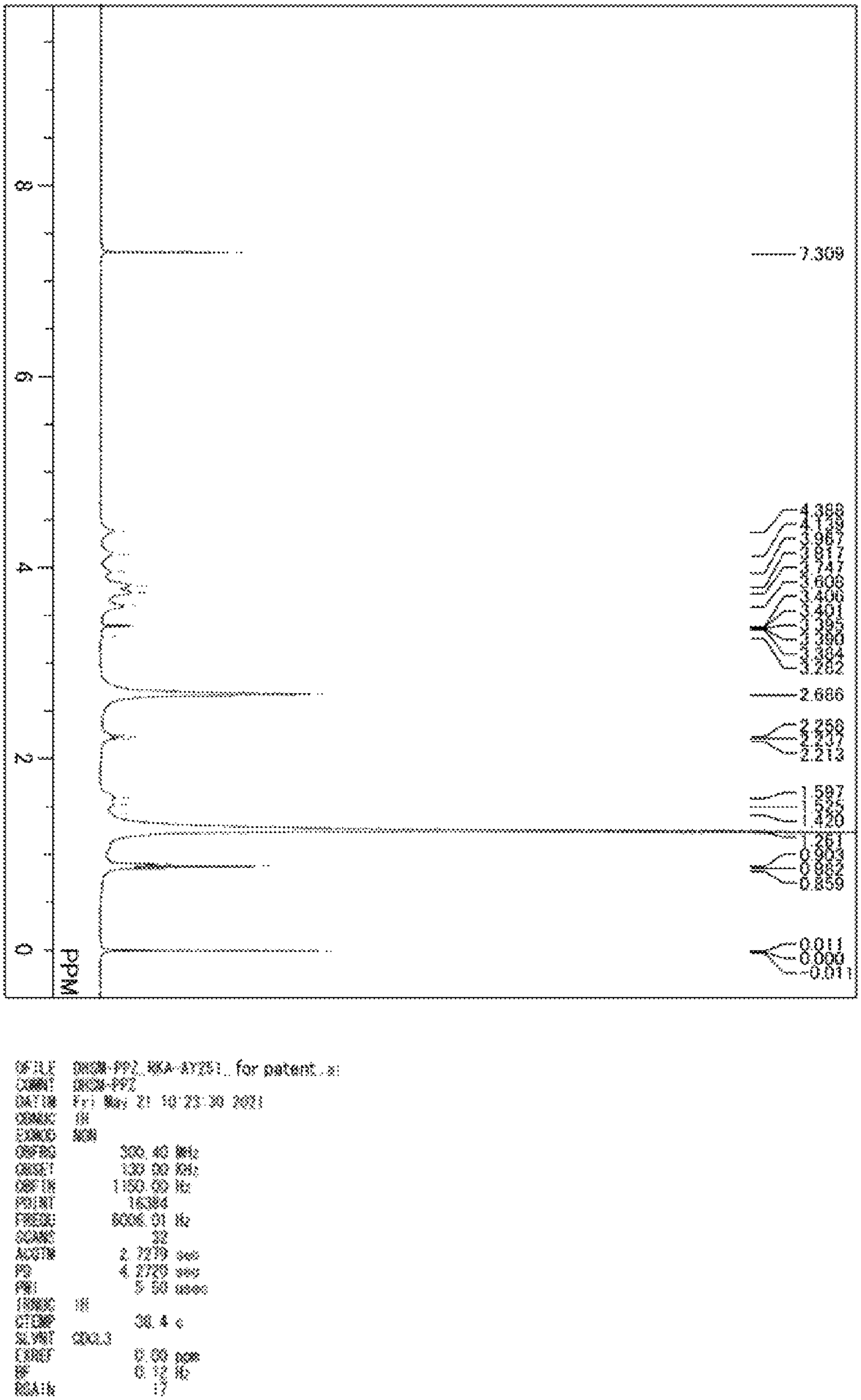
FIG. 2 shows an NMR chart of DHSM-PPZ synthesized in Example 2.

The reaction mixture was diluted with methanol and 1-butanol (methanol:1-butanol=4:1), and washed with a 20% sodium chloride aqueous solution while heating to 45° C. After extraction and washing, the organic phase was concentrated under reduced pressure, and concentrated to dryness, thereby obtaining 2.53 g of a concentrate. The obtained crude reaction product was dissolved in 25.5 mL of chloroform, methanol, and water (chloroform:methanol:water=60:30:5 (vol/vol), followed by filtration through a 0.2-μm membrane. Then, 12.7 mL of EtOH/1.25M HCl was added dropwise to the filtrate while ice-cooling, followed by stirring for 30 minutes. The white crystal precipitated after stirring was filtered, and the crystal was suspended and washed with acetone three times. The obtained crystal was vacuum-dried overnight, thereby obtaining 1.90 g of a white crystal (yield: 650). FIG. 2 shows an NMR chart.

Comparative Example 1: Synthesis of DOP-DEDA (Dioleoylphosphate-Diethylenediamine Conjugate)

DOP-DEDA was synthesized in accordance with the following scheme.

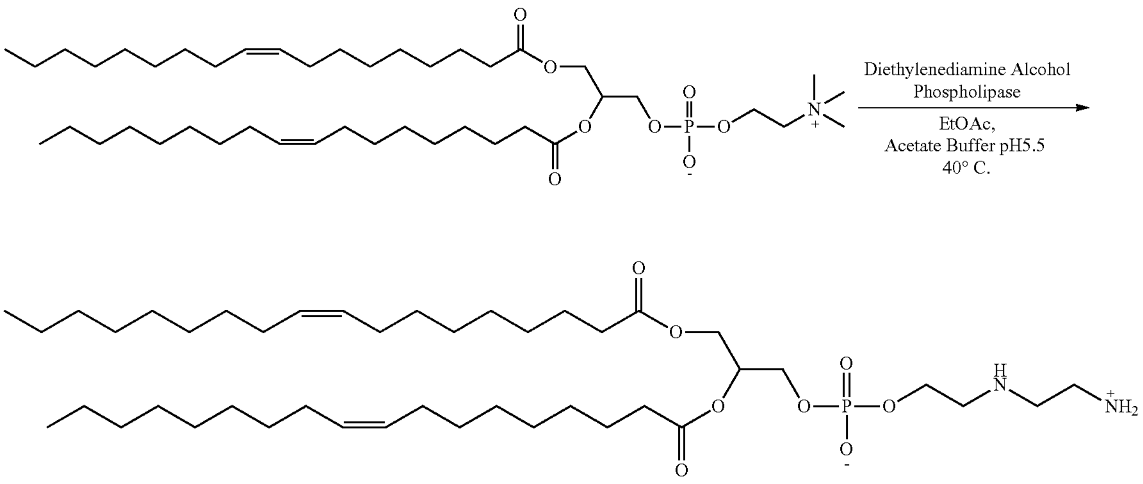

A 0.5M acetate buffer with a pH of 5.5 in which 1.84 g of 2-(2-aminoethylamino)ethanol (17.8 mmol) was dissolved was added to a mixture prepared by dissolving 1.0 g (1.3 mmol) of DOPC in ethyl acetate, and this mixture was heated to 40° C. After heating, phospholipase D (600 U) was added thereto, followed by stirring for 48 hours. The mixture was stirred until consumption of DOPC was confirmed by TLC analysis.

Figure 3:
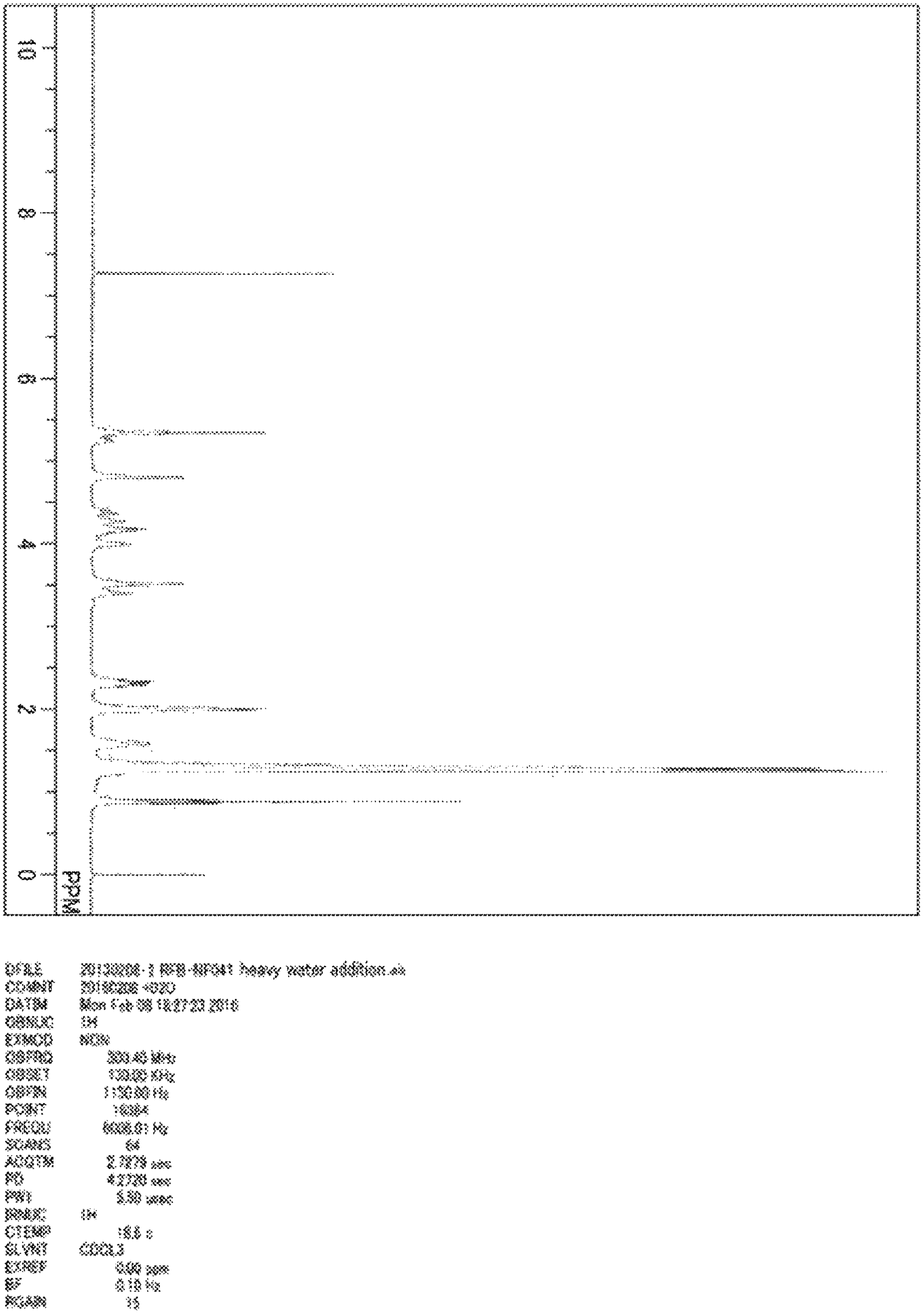
FIG. 3 shows an NMR chart of DOP-DEDA synthesized in Comparative Example 1.

The reaction mixture was diluted with chloroform and methanol (chloroform:methanol=6:1), and washed with 1'1 hydrochloric acid and a 20% sodium chloride aqueous solution. The reaction mixture was concentrated under reduced pressure, and concentrated to dryness, thereby obtaining 0.72 g of a concentrate. 0.36 g of the obtained crude reaction product was dissolved in 4 ml of dioxane, and 2 ml of dioxane/4M HCl was added dropwise thereto, followed by stirring at room temperature. After ice-cooling, acetone was added, and the mixture was stirred for 1 hour. The precipitated white crystal was suspended and washed with acetone three times. The obtained crystal was vacuum-dried overnight, thereby obtaining 0.20 g of a white crystal (yield: 40%). FIG. 3 shows an NMR chart.

Test Example 1: Production of Lipid Particles and Measurement of Various Physical Properties Test Example 1-1: Production of Lipid Particles siRNA was added to 1 mM citrate buffer (pH 4.0), thereby preparing an acidic aqueous solution of siRNA (25° C., siRNA concentration: 301.2 nM). Separately, lipids were added to ethanol, thereby preparing a phospholipid alcohol solution (25° C., lipid concentration: 2.5 mM). The molar ratios of lipids were (1) DHSM-DEDA:DHSM:cholesterol (Chol)=45:10:45, (2) DHSM-PPZ:DOPC:cholesterol (Chol)= 45:10:60, and (3) DOP-DEDA:DPPC:cholesterol (Chol)=45:10:45. A 4.15-fold volume of the acidic aqueous solution of siRNA was added to the phospholipid alcohol solution (siRNA/lipid molar ratio=1/7000), and a micro-channel (KeyChem-Basic, YMC Co., Ltd.) was used to obtain lipid particles. Finally, ethanol was removed by dialysis.

Test Example 1-2: Measurement of Various Physical Properties

The lipid particles were diluted 50-fold with RNase-free water, and then the particle size and polydispersity index (PDI) were measured with a Zetasizer Nano ZS (Malvern). The lipid particles were also diluted 50-fold with a buffer (pH=4.0, 5.0, 6.0, or 7.0), and the ζ-potential was then measured.

Further, the encapsulation efficiency of siRNA was measured in the following manner. The measurement was performed using an RNA assay reagent (RiboGreen reagent, Thermo Fisher Scientific), specifically as described below. A 2% Triton-X 100 or RNase-free water was added to a lipid particle solution. The obtained solution, RNase-free water, and a RiboGreen reagent were mixed in the wells of a 96-well black plate. The plate was shaken for 5 minutes, and the fluorescence intensity in each well was measured. The encapsulation efficiency of siRNA in the lipid particles was calculated using the following equation: the encapsulation efficiency (%)=(the fluorescence intensity of total siRNA−the fluorescence intensity of free siRNA)/(the fluorescence intensity of total siRNA), with the measured fluorescence intensity.

Figure 4:
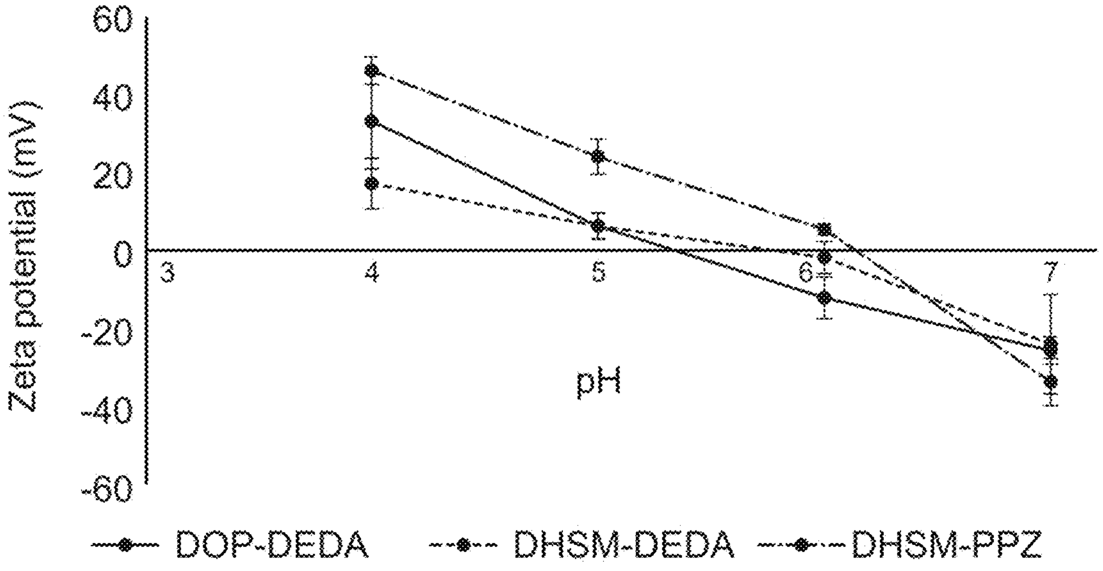
FIG. 4 shows the measurement results of the ζ-potential measured in Test Example 1-2. The legends indicate the used phospholipids A. The horizontal axis indicates the pH at the time of measurement.

Table 1 and FIG. 4 show the results.

TABLE 1

| | Particle size (nm) | PDI | Particle size distribution | siRNA encapsulation efficiency (%) |
|---|---|---|---|---|
| DOP-DEDA | 100 ± 3 | 0.11 ± 0.06 | Single peak | 98 ± 7 |
| DHSM-DEDA | 132 ± 37 | 0.09 ± 0.03 | Double peak | — |
| DHSM-PPZ | 111 ± 4 | 0.16 ± 0.01 | Double peak | 80 ± 7 |

Test Example 2: Cytotoxicity Evaluation Test

Test Example 2-1: Production of Lipid Particles

Lipid particles were produced in the same manner as in Test Example 1-1.

Test Example 2-2: Toxicity Evaluation Test

Figure 5:
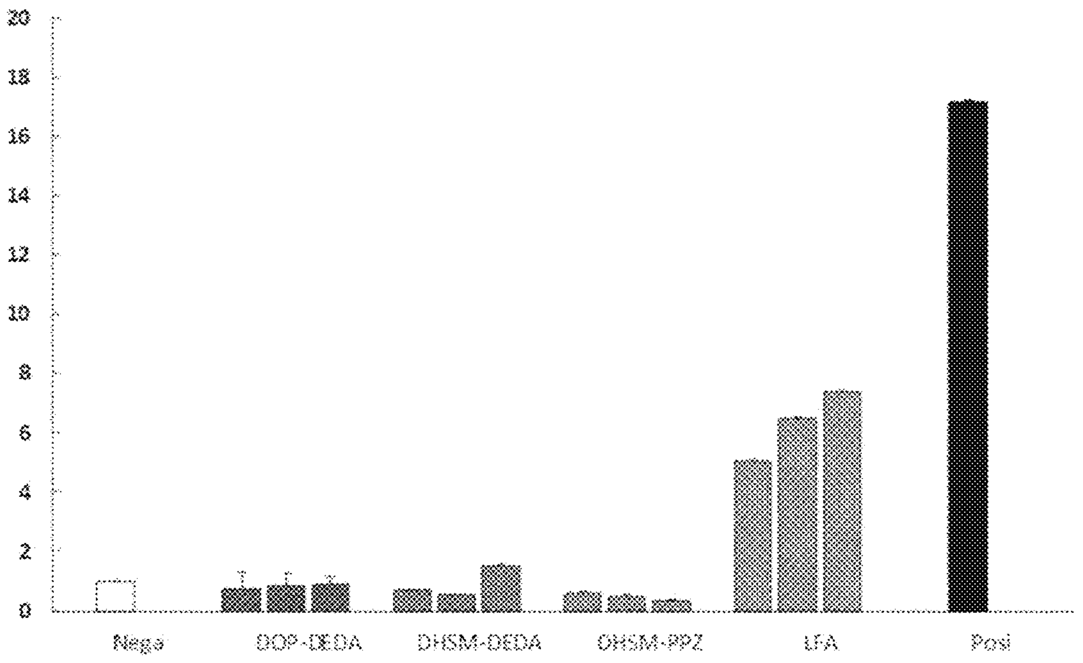
FIG. 5 shows the results of the LDH assay in Test Example 2-2.
Figure 6:
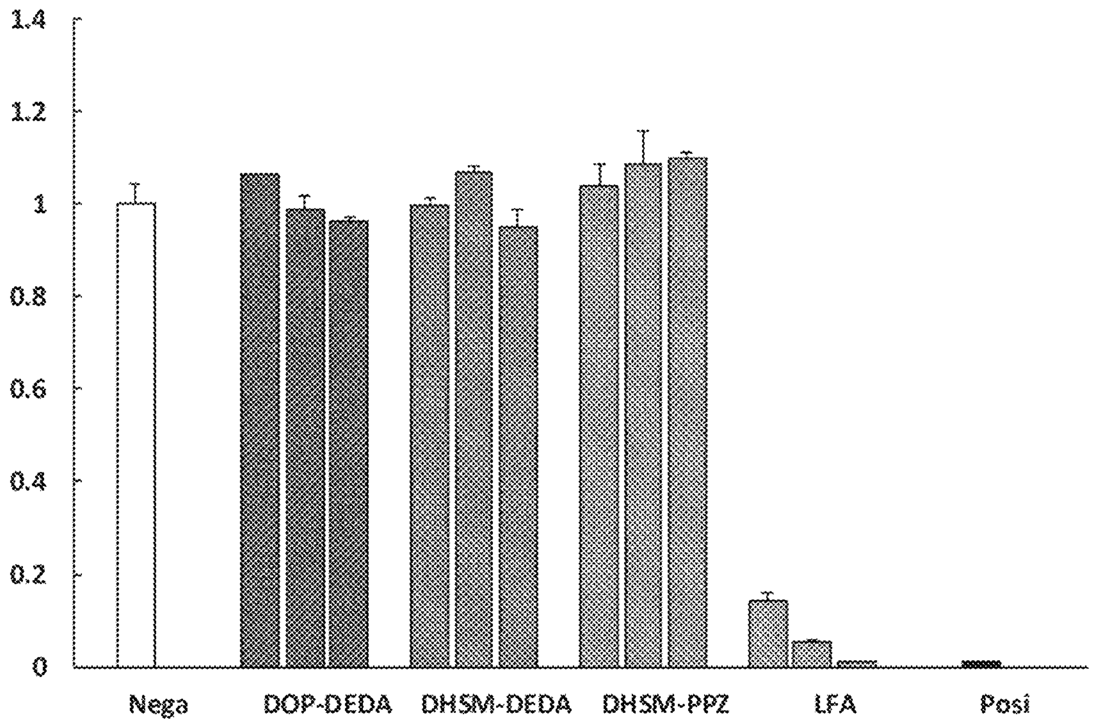
FIG. 6 shows the results of the WST-8 assay in Test Example 2-2.

MDA-MB-231 human breast cancer cells were seeded into a 96-well plate ($7\times10^3$ cells/well), and cultured at 37° C. for 24 hours. A lipid particle solution (containing 0.6/2/6 μmol of siRNA) or a lipid composite solution (containing a composite prepared using Lipofectamine (registered trademark) 2000 (Thermo Fisher Scientific), and 0.6/2/6 μmol of siRNA) was added dropwise to the wells, and the cells were cultured at 37° C. for 96 hours. The cytotoxicity of the lipid particles and lipid composite was evaluated using the Viability/Cytotoxicity Multiplex Assay Kit (Dojindo Laboratories). 20 μL of a lysis buffer was added dropwise to the wells of the positive control group, and the cells were incubated at 37° C. for 30 minutes. 100 μL of the supernatant of each well was transferred to a 96-well clear plate, and 100 μL of LDH assay reagent of the kit was added thereto, followed by incubation at room temperature for 30 minutes. Thereafter, 50 μL of a stop solution was added thereto, and the absorbance (450 nm) was measured. FIG. 5 shows the results. In addition, the medium was removed from the plate to which the cells were attached, and 120 μL of WST-8 assay reagent (Cell Counting Kit:medium=1:9) was added to each well. After incubation at 37° C. for 5 hours, the absorbance (450 nm) was measured. FIG. 6 shows the results.

In FIG. 5, which shows the results of the LDH assay, the vertical axis indicates a relative value of damaged cells when the negative control was corrected to 1, and the used phospholipids A are shown below the columns. In FIG. 5, "Nega" denotes the negative control, which is a lipid particle-free sample. "Posi" denotes the positive control, which is a lysis buffer-containing sample. "LFA" is a sample to which a lipid composite using Lipofectamine (registered trademark) 2000 was added in place of lipid particles. Three columns are shown for each sample; the three columns vary in the concentration of siRNA in the evaluation system, and the siRNA concentrations in the evaluation system are 3 nM, 10 nM, and 30 nM from left.

In FIG. 6, which shows the results of the WST-8 assay, the vertical axis indicates a relative value of damaged cells when the negative control was corrected to 1, and the used phospholipids A are shown below the columns. "Nega," "Posi," and "LFA" in FIG. 6 are the same as those in FIG. 5. Three columns are shown for each sample; the three columns vary in the concentration of siRNA in the evaluation system, as in FIG. 5, and the siRNA concentrations in the evaluation system are 3 nM, 10 nM, and 30 nM from left.

Test Example 3: Thin-Layer Chromatography (TLC) Test (Verification of Reaction Specificity)

Test Example 3-1: TLC Test of DHSM-DEDA

Figure 7:
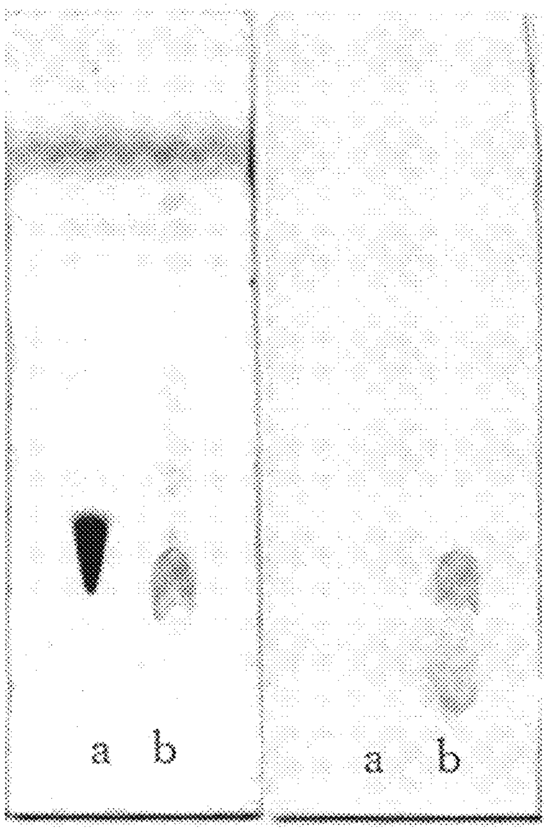
FIG. 7 shows the results of the TLC test in Test Example 3-1.

In Example 1, the stirring time after phospholipase D (1,440 U) was added was changed to 16 hours, thereby obtaining a reaction mixture containing DHSM-DEDA. Then, the reaction mixture was diluted 3-fold with a solvent of chloroform and methanol (chloroform:methanol=1:1 (volume ratio)) to prepare a diluted solution. 3 μL of the diluted solution was charged, and a TLC test was performed. The TLC plate used was TLC Silica gel $60F_{254}$ (Merck). The developing solvent used was a mixed solvent of chloroform, methanol, and water (chloroform:methanol:water=60:30:5 (volume ratio)). The color-developing agents used were copper sulfate and ninhydrin. FIG. 7 shows the results.

In FIG. 7, the TLC plate on the left side is colored using copper sulfate as a color-developing agent, and an organic compound is detected. The TLC plate on the right side is colored using ninhydrin as a color-developing agent, and an amine compound is detected. In each plate of FIG. 7, a shows the TLC test results of 50 μg equivalent of DHSM as the raw material, and b shows the TLC test results of the reaction mixture.

The results of FIG. 7 reveal that when DHSM was used as a substrate, an amine compound was detected in b of the right TLC plate, which indicates that DHSM-DEDA was sufficiently produced. Further, there were almost no organic compounds other than DHSM-DEDA in b of the left TLC plate, which indicates that the generation of impurities was suppressed. From the above, FIG. 7 demonstrated that when DHSM was used as a substrate, DHSM-DEDA was produced while suppressing the generation of impurities, and reaction specificity was excellent.

Test Example 3-2: TLC Test of DOP-DEDA

Figure 8:
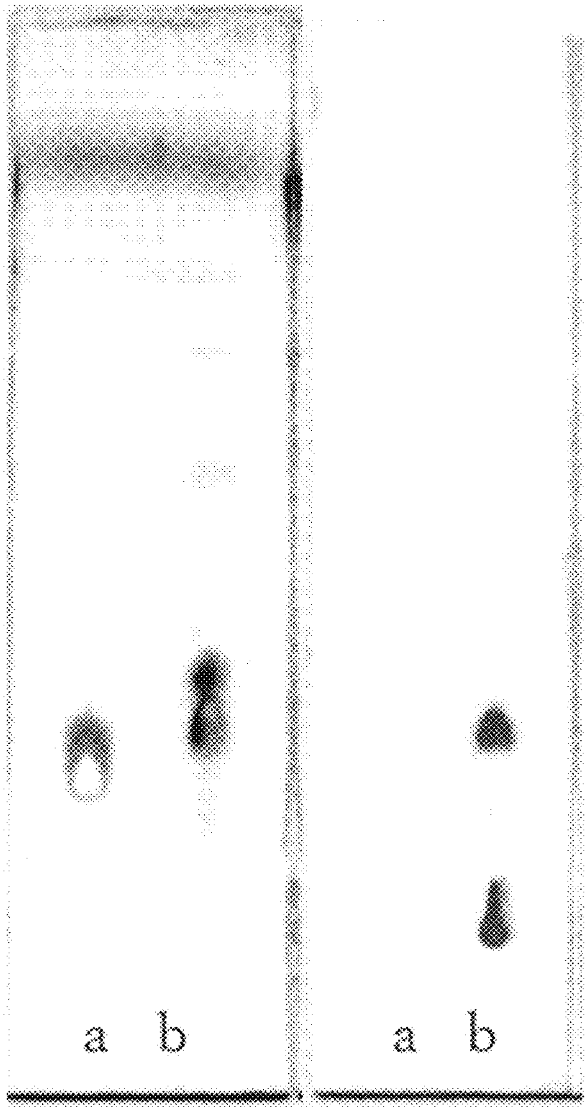
FIG. 8 shows the results of the TLC test in Test Example 3-2.

In Comparative Example 1, the stirring time after phospholipase D (600 U) was added was changed to 20 hours, thereby obtaining a reaction mixture containing DOP-DEDA. Then, the reaction mixture was diluted 3-fold with a solvent of chloroform and methanol (chloroform:methanol=1:1 (volume ratio)) to prepare a diluted solution. 3 μL of the diluted solution was charged, and a TLC test was performed. The TLC plate used was TLC Silica gel $60F_{254}$ (Merck). The developing solvent used was a mixed solvent of chloroform, methanol, and water (chloroform:methanol:

water=60:30:5). The color-developing agents used were copper sulfate and ninhydrin. FIG. 8 shows the results.

In FIG. 8, the TLC plate on the left side is colored using copper sulfate as a color-developing agent, and an organic compound is detected. The TLC plate on the right side is colored using ninhydrin as a color-developing agent, and an amine is detected. In each plate of FIG. 8, a shows the TLC test results of 50 μg equivalent of DOPC as the raw material, and b shows the TLC test results of the reaction mixture.

The results of FIG. 8 reveal that when DOPC was used as a substrate, an amine compound was detected in b of the right TLC plate, which indicates that DOP-DEDA was sufficiently produced. On the other hand, organic compounds other than DOP-DEDA were also detected in b of the left TLC plate, which indicates that the generation of impurities was not suppressed. From the above, FIG. 8 demonstrated that when DOPC was used as a substrate, DOP-DEDA was not sufficiently produced, the generation of impurities was not suppressed, and reaction specificity was inferior.

The invention claimed is:

1. A phospholipid represented by formula (1):

(1)

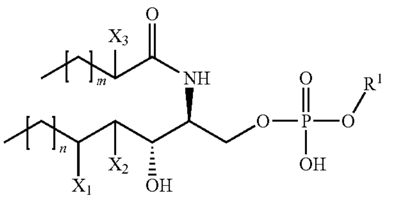

wherein m represents a natural number of 9 to 25, n represents a natural number of 10 to 15, $X_1$, $X_2$, and $X_3$ are the same or different and each represent H or OH, and $R^1$ represents the following formula (i) or (ii):

(i)

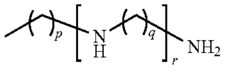

wherein p represents 1 or 2, q represents 1 or 2, and r represents an integer of 1 to 4; or (ii)

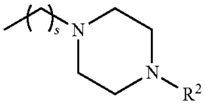

wherein s represents an integer of 1 to 3, and $R^2$ represents a hydrogen atom or a hydrocarbon group.

2. The phospholipid according to claim 1, wherein m represents a natural number of 13 to 21, and n represents a natural number of 11 or 12.

3. The phospholipid according to claim 1, represented by the following formula (2):

(2)

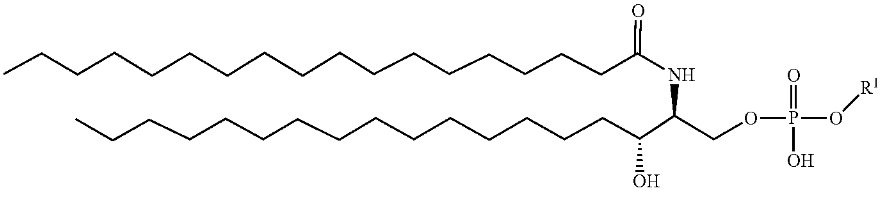

wherein $R^1$ is as defined above.

4. A lipid particle comprising the phospholipid according to claim 1.

5. The lipid particle according to claim 4, in which a medicinal substance is encapsulated.

6. The lipid particle according to claim 5, wherein the medicinal substance is a polynucleotide.

7. The lipid particle according to claim 4, comprising a sterol.

8. The lipid particle according to claim 4, further comprising a additional phospholipid.

9. An alcohol solution comprising the phospholipid according to claim 1.

10. The alcohol solution according to claim 9, wherein an alcohol in the alcohol solution is ethanol.

11. A method for producing a lipid particle, the method comprising mixing the alcohol solution according to claim 9 with an acidic aqueous solution.

12. A medical drug comprising the lipid particle according to claim 4.

* * * * *